United States Patent
Haynes et al.

(10) Patent No.: US 8,653,937 B2
(45) Date of Patent: *Feb. 18, 2014

(54) SYSTEM AND METHOD FOR PROSTHETIC/ORTHOTIC DEVICE COMMUNICATION

(75) Inventors: Michael L. Haynes, Bexley, OH (US); Derek Matthew Nixon, Grove City, OH (US)

(73) Assignee: The Ohio Willow Wood Company, Mt. Sterling, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/584,474

(22) Filed: Aug. 13, 2012

(65) Prior Publication Data

US 2012/0299696 A1  Nov. 29, 2012

Related U.S. Application Data

(63) Continuation of application No. 12/052,729, filed on Mar. 20, 2008, now Pat. No. 8,242,879.

(51) Int. Cl.
*A61B 5/07* (2006.01)
*H04B 1/38* (2006.01)
*G09B 21/00* (2006.01)

(52) U.S. Cl.
USPC ....... 340/4.1; 340/4.11; 340/4.61; 340/12.22; 340/12.5; 340/573.1

(58) Field of Classification Search
CPC ............ A61B 5/07; A61B 19/00; H04B 1/38; G09B 21/00
USPC ........... 340/4.1, 4.11, 4.61, 4.62, 12.22, 12.5, 340/13.24, 573.1, 539; 128/897; 455/73, 455/502; 704/271, 231; 600/302
See application file for complete search history.

(56) References Cited

U.S. PATENT DOCUMENTS

| | | | | | |
|---|---|---|---|---|---|
| 4,284,856 | A | * | 8/1981 | Hochmair et al. | 607/9 |
| 5,413,611 | A | * | 5/1995 | Haslam et al. | 623/25 |
| 6,198,394 | B1 | * | 3/2001 | Jacobsen et al. | 340/573.1 |
| 6,400,990 | B1 | * | 6/2002 | Silvian | 607/60 |
| 6,834,436 | B2 | * | 12/2004 | Townsend et al. | 33/512 |
| 7,171,166 | B2 | * | 1/2007 | Ng et al. | 455/73 |
| 7,676,372 | B1 | * | 3/2010 | Oba | 704/271 |
| 7,794,499 | B2 | * | 9/2010 | Navarro et al. | 623/17.11 |
| 2001/0014441 | A1 | * | 8/2001 | Hill et al. | 434/236 |
| 2005/0283257 | A1 | * | 12/2005 | Bisbee et al. | 623/24 |
| 2006/0005845 | A1 | * | 1/2006 | Karr et al. | 128/897 |
| 2007/0158911 | A1 | * | 7/2007 | Torre | 273/317 |
| 2008/0161660 | A1 | * | 7/2008 | Arneson et al. | 600/302 |

* cited by examiner

*Primary Examiner* — Nam V Nguyen
(74) *Attorney, Agent, or Firm* — Standley Law Group LLP

(57) ABSTRACT

A system and method for prosthetic/orthotic (PO) device and/or PO system communication. PO devices of the present invention may employ common communications and/or communications/control modules that allow for wireless communication between PO devices and other devices, such as remote controls and data transfer devices. The present invention also provides for a methodology of determinant and non-interfering simultaneous communication between multiple PO devices of a PO system.

20 Claims, 9 Drawing Sheets

| Frequency designation | A | B | C | D | E | F | G | H | I | J | K | L | M | N | O | P | Q | R | S | T |
|---|---|---|---|---|---|---|---|---|---|---|---|---|---|---|---|---|---|---|---|---|
| Device 1 | X→ | | | | | | | | | | | | | | | | | | | |
| Device 2 | | | | | X→ | | | | | | | | | | | | | | | |
| Device 3 | | | | | | | | | X→ | | | | | | | | | | | |
| Device 4 | | | | | | | | | | | | | X→ | | | | | | | |
| Device 5 | | | | | | | | | | | | | | | | | X→ | | | |

FIG-6

SYSTEM AND METHOD FOR PROSTHETIC/ORTHOTIC DEVICE COMMUNICATION

The present application is a continuation of U.S. patent application Ser. No. 12/052,729, filed on Mar. 20, 2008.

BACKGROUND

The present invention is directed to a system and method for interfacing/communicating with a prosthetic/orthotic device or accessory and for the collection, processing, display, storage, and/or management of data related thereto. More particularly, present invention is directed to a system and method for interfacing with and performing one or more such functions with respect to a single prosthetic/orthotic device or accessory or to a number of prosthetic/orthotic devices and/or accessories of a prosthetic/orthotic system. Certain embodiments of the present invention may also be capable of programming, configuring, testing and/or evaluating prosthetic/orthotic devices and/or accessories of a prosthetic/orthotic system. Data relating thereto may be communicated via various tools and/or reports to a patient, prosthetist, orthotist, and/or others.

As the degree of technical sophistication of prosthetic and/or orthotic devices (hereinafter "PO devices") and accessories advances, the need to provide users with the ability to monitor and/or control such PO devices increases. While simple remote controls and other interface devices capable of allowing access to a single PO device are known, utilizing this method of communication in the case of multiple PO devices would require the carrying and use of multiple remote controls/interfaces. Obviously, this is not a practical solution. Further, systems comprising multiple PO devices, i.e., prosthetic and orthotic systems (hereinafter "PO systems"), have become more complex. As such, the need to enable individual PO devices to interact not only with a user, but also with each other, has also become more important.

It would be understood by one skilled in the art that there a considerable number of PO devices in existence. Many other PO devices are undoubtedly in development, or will be developed in the future. Such PO devices will likely continue to increase in complexity. Thus, it can also be understood that there are a multitude of parameters that are, may be, and/or should be, monitored and evaluated during use of such PO devices.

Such a large array of PO devices and parameters advantageously allows for a wide range of PO system designs and configurations (depending on the deficit pattern presented by a given patient). However, as such PO systems become more complex, the number of associated parameters that should be monitored and evaluated greatly increases. Further, the parameters of individual PO devices may affect or depend on the parameters of one or more other individual PO devices when used in a PO system. For at least these reasons, it has become highly desirable, if not necessary, to reevaluate the mechanisms and methods of communication with individual PO devices, as well as with and between PO devices of PO systems.

It is possible to provide access to one or more PO devices with a device such as a known hand held remote control. However, the level of sophistication of current and future PO devices would render it difficult, if not impossible, to fully realize the configuration, optimization, and/or feedback possibilities afforded by such PO devices and PO systems when using such a simplistic interface mechanism. Therefore, it would be beneficial to provide a clinician and/or other interested parties with patient tools that will allow for a more complete and organized ability to create useful configurations and access device and system data relating thereto.

Providing such tools is a technically challenging proposition, however. For example, in a very simple exemplary application, a single remote control device may communicate with a single evacuation device of a prosthesis having a vacuum suspension system. This may allow for functions such as monitoring the state of charge of a power source associated with the evacuation device, adjusting vacuum levels, and activation/deactivation of the evacuation device and/or other related components. In a more complicated system, a similar remote might communicate with two prosthetic legs which, in turn, communicate with each other and with a personal computer. With respect to communication with a personal computer, the timing of the communications may only need to be time stamped in some manner so that it could be reconstructed at a later time. The data communicated to the remote control may not be time sensitive at all. However, the communication timing between the two prosthetic limbs would need to be determinant so that the control data passed therebetween could be used for timing sensitive control functions. Consequently, it is important to realize that in order for the data between the two exemplary prosthetic legs to be temporally determinant, all the communications between all the PO devices associated therewith will need to comply with enforced communication timing.

Unfortunately, many standard network protocols cannot or do not enforce such communication timing. In effect, most protocols simply assure that a message sent will arrive at its destination—but not mandate when the message will arrive. Further complicating matters, is the fact that most PO systems are battery powered and, therefore, are very sensitive to power consumption. Therefore, while a known and common method for enabling the transmission of time critical messages is to continuously maintain an open high-speed communications link, this is not practical in the case of a battery-powered PO device which must talk to multiple other PO devices.

Furthermore, as more and more consumer electronic devices embrace wireless communication technologies, it becomes increasingly likely that multiple devices in a given location will be simultaneously communicating using wireless devices that transmit in the same frequency band. As a result, interference and possible eavesdropping become a potential problem. In the case of PO devices, where reliability and privacy are both significant concerns, this issue must also be addressed.

As PO devices and PO systems become more sophisticated, they gain desirable capabilities. However, these added capabilities come at the cost of added complexity. Therefore, proper adjustment, maintenance, and monitoring of PO devices and PO systems comprised thereof, may require the evaluation of significant amounts of data. To properly enable access to and use of such data, it would be useful to provide tools that simplify these tasks.

It would be apparent to one skilled in the art that the ability to remotely interface with a PO device(s) is desirable for many reasons. However, as PO systems are generally configured for a particular patient, it is obvious that the settings in which PO devices and PO systems are used may vary greatly. Consequently, remote control devices for use as described herein may require different types of interfaces for different types of PO devices. To provide for this ability, it would be desirable for such a remote control device to have at least certain components that are of an easily reconfigurable design.

As noted previously, microprocessor-controlled and/or other modern PO devices offer a great amount flexibility in PO system design, as well as the ability to monitor, collect and report a wide range of data applicable to the use thereof. Prosthetic/orthotic components such as for example, prosthetic sockets, typically have many variable parameters associated therewith. A complete prosthesis/orthosis may have several such components. Human factors such as weight, height, activity level, etc., may also vary considerably from patient-to-patient and from prosthesis-to-prosthesis. Consequently, simple measurement of parameters such as vacuum level, vacuum variation, cadence, etc., may not necessarily allow a clinician to adequately evaluate or adjust the performance of a PO device or PO system. It can be understood, therefore, that the data provided by PO devices may be extremely useful with respect to determining and/or optimizing the fit, performance, etc., of a PO device or PO system. As such, and because the amount of data recorded by a PO device between visits to a clinician may be quite significant, it would be useful to allow a clinician or another user to download data from a PO device or one or more PO devices of a PO system to another device for documentation, viewing and analysis.

SUMMARY

The present invention satisfies the needs and desires described above. The present invention allows for remote, efficient and adaptable communication with one or more PO devices. The present invention also provides for a methodology by which multiple PO devices may communicate with each other without interference, and in a manner by which data transmitted from a PO device can be used in substantially real time to optimize its function, the function of one or more other PO devices, or the function of an entire PO system. The present invention also provides for the ability to record and collect useful data regarding one or more PO devices or a PO system, and to optionally store, and transmit or otherwise transfer said data to another device for viewing and analysis.

With respect to the present invention, it is to be understood that a prosthetic device may include, but is not limited to, a replacement limb or joint such as a foot, ankle, knee, hip, shin, thigh, hand, wrist, elbow, shoulder or arm, a prosthetic component such as a socket, liner, sleeve, or suspension mechanism, and/or a sensor such as a Electromyogram (EMG) sensor, pedometer, activity level monitor, inertial sensor, pressure sensor, force sensor, accelerometer, generator, heart rate monitor, or the various communications devices introduced in this application. Similarly, an orthotic device may include, but is not limited to an orthosis designed for foot, ankle-foot, knee-ankle-foot, knee, wrist, elbow, shoulder, spinal neck, or cranial application. Also for the purposes of the present invention, parameters detected or measured by sensors or other devices may include, without limitation, stiffness, angle, displacement, velocity, acceleration, force, moment, volume, pressure, temperature, time, heart rate, current, voltage, charge level, and perspiration (presence or level). One skilled in the art would realize that the aforementioned listing of devices and parameters is merely exemplary, not exhaustive, and various other devices and/or parameters would also fall within the scope of the present invention.

PO devices of the present invention in general, as well as communications and control sections of such PO devices, are preferably highly configurable in nature. In this manner, a single remote control or PO device can be configured to function within a nearly unlimited number of PO system architectures. To facilitate such configurability, PO devices and PO systems of the present invention preferably employ microprocessor-controlled communications devices.

Preferably, the microprocessor-controlled communications devices of the present invention are modular in nature. That is, a communications module of the present invention is preferably comprised of a communication device (i.e., transceiver) and an associated microprocessor mounted to module board. Optionally, the communications module may also include a power supply, such as a regulator. The communications module can then be attached to a host board specifically designed to provide particular functions appropriate to an associated PO device. Preferably, the same communications module may be utilized in other devices of the present invention, as described in more detail below.

It is to be understood that while a microprocessor-controlled communications device of the present invention is referred to above and hereafter as a "communications module," such a device may actually perform both communication and control functions with respect to a PO device to which it is installed. Thus, while the term "communications module" is used herein for purposes of brevity, nothing herein is to be interpreted as limiting the capabilities of such a module to communication functions only.

The aforementioned clarification notwithstanding, it is in fact possible that a more complex PO device, such as a prosthetic limb, might require more processing power than would be practical to include on a communications module. In such a case, the microprocessor of the communications module may be used to mediate communications with external devices, while a host processor would oversee functions of the associated PO device.

Communication by a user (e.g., clinician and/or patient) with a PO device or with multiple PO devices of a PO system is preferably accomplished remotely. To that end, the present invention makes use of remote control devices that preferably include the same communications module present in the PO devices. When used in a remote control device of the present invention, the communications module is again mounted to a host board that may include other components such as without limitation, a display, a keypad, a USB connector, etc. Preferably, the module and host board are mounted within a housing that also contains a power source. The remote control may take the form of a FOB.

As PO systems are generally configured for a specific patient, a remote control of the present invention is preferably of flexible design. For example, a remote control may allow for the use of interchangeable interfaces that can be selected based on the particular type(s) of PO devices with which the remote control will be used. Such flexibility may specifically include, but is not limited to, the use of a flexible software environment that allows a remote control to execute different programs for interfacing with different devices—without changes to the hardware; a configurable key pad that can easily be changed; a variety of display types that can convey a range of information, and do so in a manner that is useful to users who may have compromised visual acuity; an easily replaceable, or rechargeable power source; and/or a backlit display with, optionally, adjustable intensity, so that the remote control can be used in the dark without consuming valuable battery power under daylight or otherwise illuminated conditions.

Because PO devices of the present invention may store potentially large amounts of useful data, the present invention also contemplates the use of a data transfer device through which such data can be transferred to another device (e.g., a PC) for viewing and analysis.

One method of implementing such a device is to mount a communications module to a host board and to incorporate a USB interface onto the host board. This allows the data transfer device to be connected to a PC, a Personal Digital Assistant (PDA), or another device equipped with a USB port. The communications module then provides for wireless communication between the PO device(s) and the data transfer device, wherein the communication protocol is converted to serial form for compatibility with a PC, PDA, or other digital device.

As described above, when multiple PO devices are used simultaneously to create a PO system, various communications-related problems may occur. In order to circumvent such problems, the present invention may enforce communication timing, while also minimizing power consumption, by utilizing the concept of time slicing. While this method is normally applied to managing CPU multitasking, it also provides significant benefits for a communication protocol useable in the present invention. In the case of a PO system operating under this protocol, time is broken up into periods assigned to specific PO devices. The total period time will generally depend on the update rate necessary for the given PO system. This time period is then broken up into a number of time slices according to the bandwidth required by each PO device pairing.

Further, the present invention may require PO devices operating under the above described time slice protocol to continuously switch (hop) operating frequencies. In the event of interference, a PO device is thereby afforded multiple opportunities within each time slice to establish communication. If a frequency hopping period is short enough to result in numerous hops inside of a single communication time slice, every communication in every time period can be tried on multiple frequencies to ensure that the communication will get through. One possible implementation of such a protocol might be in a PO system comprising numerous PO devices that are associated with multiple prosthetic limbs worn by a single patient.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 3b is a schematic diagram representing the remote control of FIG. 3a;

FIG. 6, graphically illustrates the PO devices of FIG. 5 employing a frequency hopping communication timing protocol so as to avoid interfering communications.

DETAILED DESCRIPTION OF EXEMPLARY EMBODIMENT(S)

PO Devices

Figure 1:
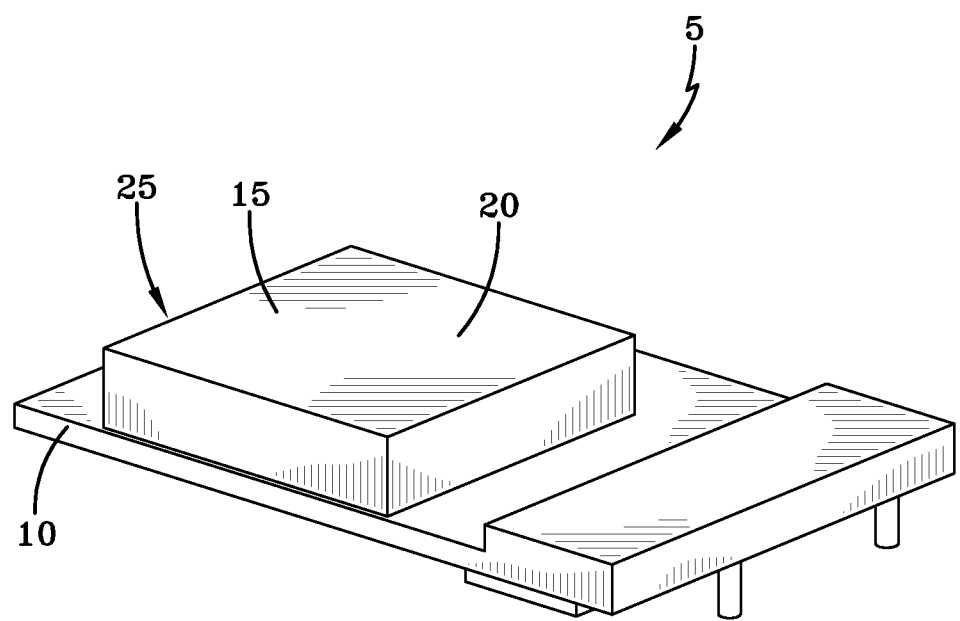
FIG. 1 is a basic representation of a communication module of the present invention.

As described above, various devices of the present invention are preferably at least partially modular in nature. To that end, one exemplary communications module of the present invention is illustrated in FIG. 1. As shown in FIG. 1, the communications module 5 includes a module board 10 to which is mounted a microprocessor 15 and a transceiver 20. While the transceiver portion of such a communications module could use acoustic, optical, or electrical technologies, such embodiments would require a user to touch a remote control to an associated PO device in order to activate the communications module. Consequently, the transceiver is preferably a radio transceiver.

In the particular embodiment shown, the microprocessor 15 and the transceiver 20 are integrated into one chip 25. It has been found that the CC2511 and CC2512 microprocessor controlled transceiver chips from Texas Instruments are especially well-suited for this purpose. Alternatively, one skilled in the art would certainly realize that is also possible to create a communications module according to the present invention wherein a separate microprocessor and transceiver are employed. For example, a Texas Instruments CC 2500 transceiver may be used in combination with a Texas Instruments MSP430 series microprocessor in such an embodiment. While the use of a chip having an integrated microprocessor and transceiver allows for a significant reduction in the size of a communications module of the present invention, it has been found that such an embodiment does consume more power than an embodiment employing separate microprocessor and transceiver components.

As mentioned above, when used in simple PO devices, the microprocessor of a communications module could also be used to control the PO device. For example, such functionality may occur in PO devices such as remote controls, computer interfaces, vacuum suspension system components (e.g., an evacuation device). In more complex designs, this microprocessor of a communications module could be relegated to a communications interface between a main control device and the transceiver.

Figure 2A:
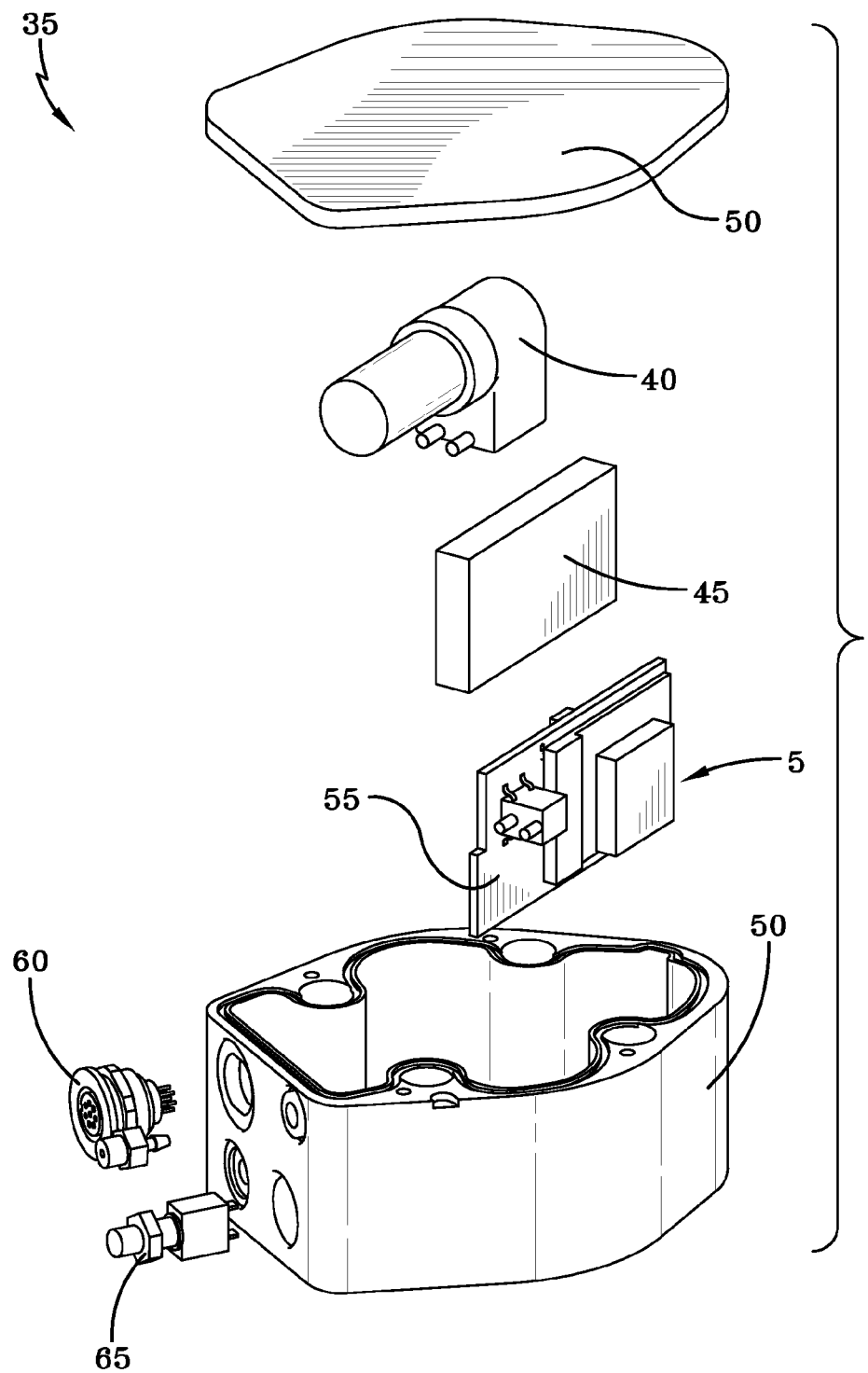
FIG. 2a illustrates one exemplary embodiment of a PO device of the present invention, in the form of a prosthetic socket evacuation device.
Figure 2B:
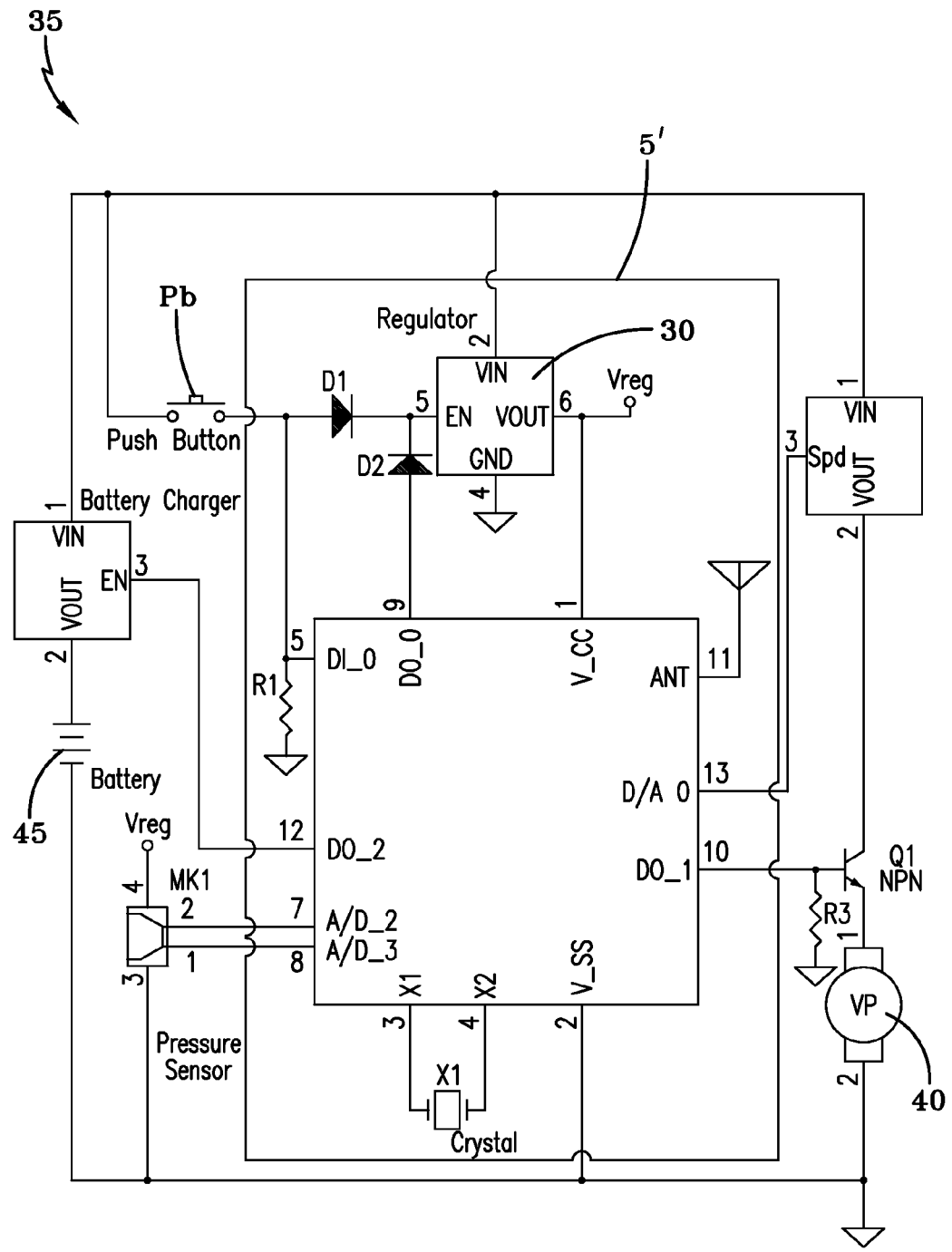
FIG. 2b is a schematic diagram representing the evacuation device of FIG. 1.
Figure 3A:
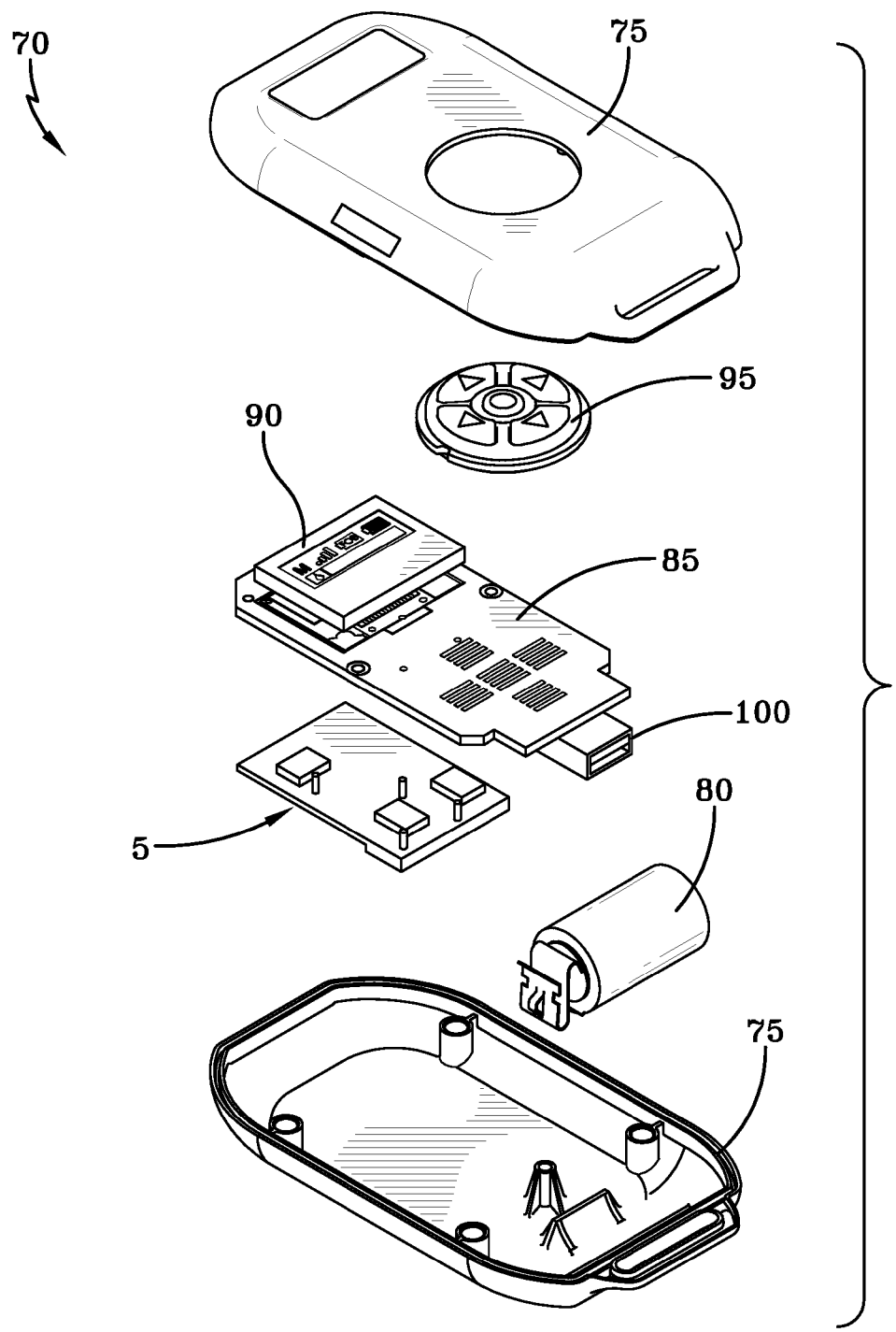
FIG. 3a depicts one exemplary embodiment of a remote control device of the present invention, in the form of a FOB.
Figure 3B:
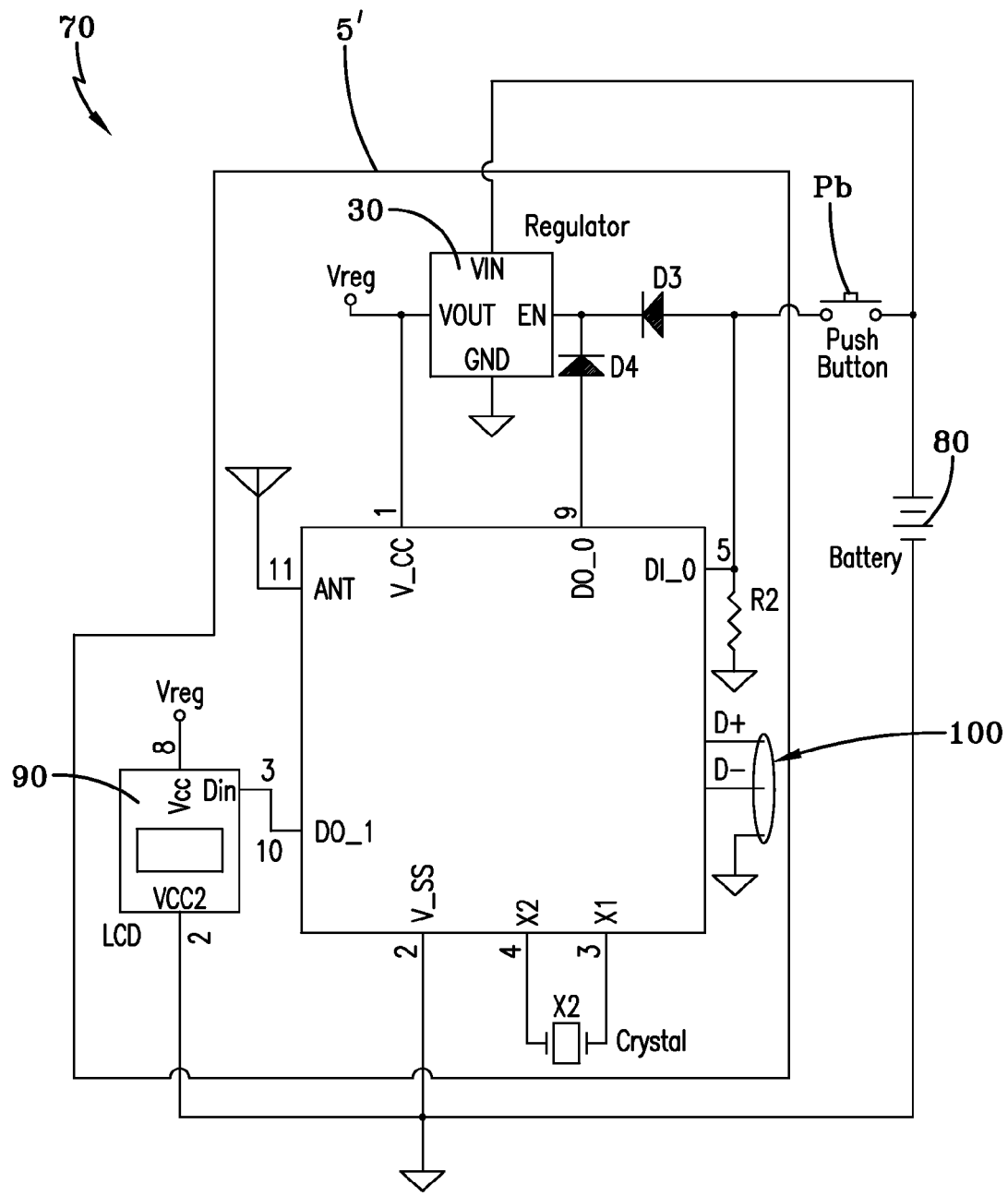

An alternate embodiment of a communications module 5' of the present invention is indicated by the dashed boundary of FIGS. 2b and 3b. This communications module is essentially the same as the communications module 5 of FIG. 1, except for the addition of a power source. In this particular embodiment, the power source is a regulator 30. The use of the regulator 30 represents one possible improvement on the basic communications module design of FIG. 1. While not necessary to a communications module of the present invention, the addition of the regulator 30 can be desirable for several reasons. First, the regulator 30 provides a ready source of regulated power for simple host boards. Second, the use of the regulator 30 allows the microprocessor 15 to shut itself and other hardware off to save power when all necessary tasks are complete. Preferably, the regulator 30 is latched by the microprocessor 15.

As shown in FIGS. 2b and 3b, output port DO_0 from a microprocessor 15' and a push button PB of an associated PO device are both able to energize an enable pin EN on the regulator 30. The latching function is then implemented in firmware. Function progresses as follows: a user pushes the pushbutton PB; power from the pushbutton enables the regulator 30 and the regulator turns on; the microprocessor 15' powers up; the microprocessor turns on output port DO_0; when the pushbutton is released, the enable pin EN on the regulator is still held high by the microprocessor, latching the regulator on; the microprocessor holds the enable pin high until all processes are complete, and then pulls the enable pin low to shut down the regulator. As a result, the microprocessor 15' itself and any other hardware powered by the regulator 30 is also shut down.

If the regulator 30 is chosen for low quiescent current and low leakage when off, it is possible to eliminate nearly all power normally lost due to regulator functions. This extends battery life when an associated PO device is active, and prevents discharge when the PO device is off. The MAX8880 series of regulators made by Maxim Integrated Products Inc., has been found to be particularly suitable for this application. In this device, quiescent current when the regulator is active is guaranteed to be below 10 uA and leakage when the regulator is off is guaranteed to be below 3 uA. For reference, if the regulator is left active, with no load, and powered with a 600 mAh battery, the regulator would not discharge the battery for nearly 7 years. In fact, this means that the internal leakage in the battery would most likely become the primary factor in battery life.

Figure 4:
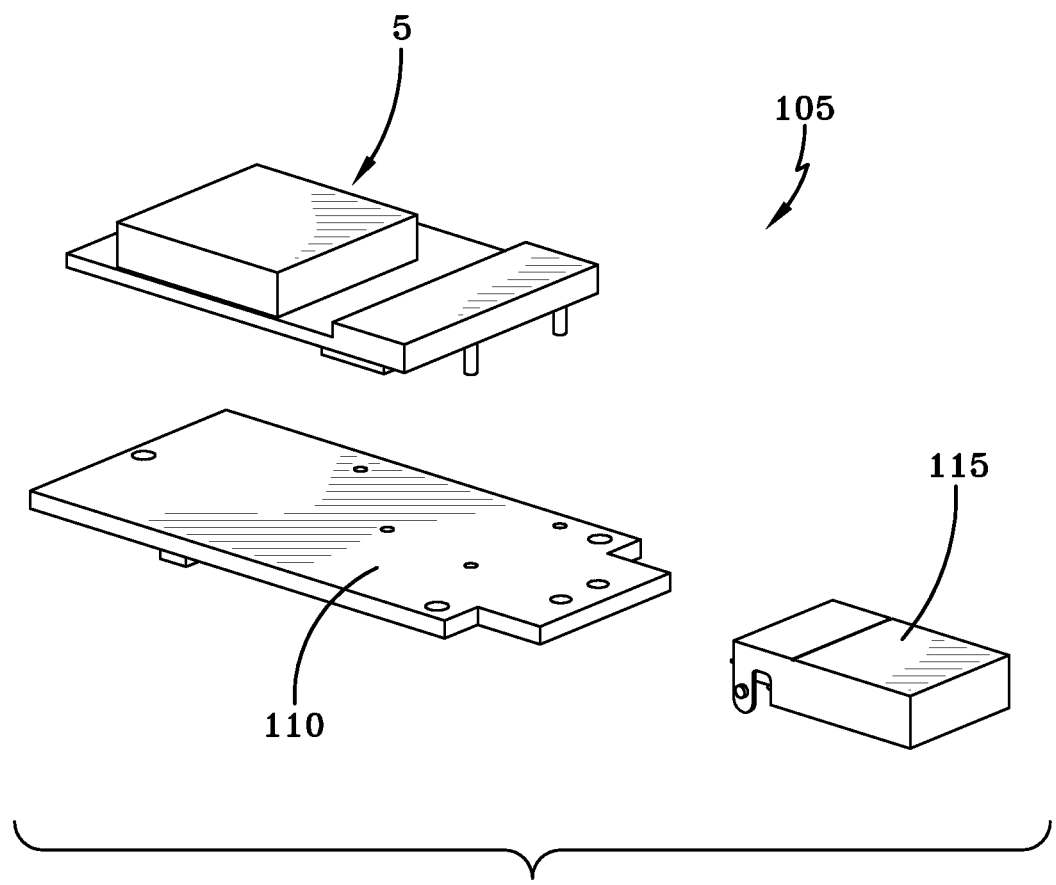
FIG. 4 represents one exemplary embodiment of a data transfer device of the present invention.

A communications module of the present invention is designed to be used in a variety of different PO devices by connection to and communication with a number of different host boards (see FIGS. 2-4). In this manner, a multitude of different PO devices may employ the same communications module. The use of a common communications module is beneficial for several reasons including for example, a resulting reduction in time and costs associated with research and development and manufacturing, a reduction in necessary service parts, and an increased familiarity of design amongst clinicians and other users and/or service personnel associated with PO devices in which such communications modules are used. Furthermore, as such communications modules require approval by the FCC, the design and use of a common and FCC-approved communications module eliminates the time-consuming task of repeatedly enduring the FCC approval process.

As described in more detail below and as illustrated in FIGS. 2-4, exemplary embodiments of PO devices employing a communications module of the present invention may include, without limitation, an evacuation device of a vacuum suspension system, a remote control, and a data transfer device. As shown, each of these PO devices includes the same communications module 5', which is essentially the same communications module 5 shown in FIG. 1, except for the addition of the regulator 30.

A PO device comprising an evacuation device 35 of a vacuum suspension system is depicted in FIGS. 2a-2b. Such an evacuation device 35 is typically used to evacuate the interior of a prosthetic socket portion of a prosthesis. As shown, this particular evacuation device 35 is designed for attachment to a distal exterior end of a prosthetic socket, but a number of also designs are also possible.

The evacuation device 35 can be seen to include a vacuum pump 40, a power source (e.g., battery) 45 and a housing 50. The evacuation device 35 also includes a communications module 5', but could also include a communications module without a power supply, such as the communications module 5 of FIG. 1. The communications module 5' is connected to a host board 55. The host board 55 also includes other components that are provided to perform or permit various functions associated with the evacuation device 35. For example, the host board 55 may include controls for the vacuum pump 40 and for a vacuum sensor (not shown). Each of the communications module 5', vacuum pump 40, power source (e.g., battery) 45 and host board 55 are designed to reside within the housing 50. In this particular embodiment, the evacuation device 35 also includes an optional programming and charging port 60 and a push-button interface 65.

Another PO device, in the form of a remote control 70, is shown in FIGS. 3a-3b. In this particular embodiment, the remote control 70 is in the form of a small FOB, but various other sizes and configurations are obviously also possible.

As shown, the remote control 70 includes a housing 75, for enclosing at least some of the other components of the remote control. A power source 80 (e.g., a battery) is present to provide power to the remote control 70. The remote control 70 includes the communications module 5 of FIG. 1 (but shown in an inverted orientation), but could also include a communications module having a power supply, such as the communications module 5' of FIG. 2b. The communications module 5 is connected to a host board 85. The host board 85 also includes other components that are provided to perform or permit various functions associated with the remote control 70. For example, and without limitation, the host board 85 may include a display 90 for providing various information to a user and a keypad 95 that is accessible through the housing 75 for entering data, commands, etc., into the remote control.

When present, the display 90 may be of virtually any type known to those of skill in the art. However, a display of the LCD variety may be especially attractive in this application due to the low power consumption characteristics associated therewith. The display 90 may also be of virtually and size and shape. As mentioned above, the display 90 may also be backlit and have, optionally, adjustable intensity, so that the remote control 70 can be used in the dark without consuming valuable battery power under daylight or otherwise illuminated conditions.

When present, the keypad 95 may also be of virtually any type known to those of skill in the art. Preferably, but not necessarily, the keypad 95 is easily interchangeable with other keypads to facilitate the creation of customized and device-appropriate remote controls.

For at least the reasons described in more detail below, the particular remote control 70 of FIGS. 3a-3b is shown to include an optional USB port 100. The presence of the USB port 100 provides for the possibility of connecting any number of USB compatible devices to the remote control 70. For example, a typical USB flash drive may be connected to the remote control to receive an upload of data therefrom. It may also be possible to transmit data from a PO device to the remote control 70 where it can be saved on a flash drive or similar USB-compatible storage device docked to the USB port 100. The flash drive could then be transported to another device for viewing and/or analysis. Via such an embodiment, it may be possible for example, to have a patient upload data from the remote control 70 and/or a PO device in communication therewith to a flash drive or similar USB-compatible data storage device and subsequently send the storage device to a clinician for evaluation at a remote location. Similarly, a clinician, a PO device part manufacturer, etc., could provide a user of the remote control 70 with a USB-compatible storage device loaded with data (e.g., PO device programming instructions, an upgraded BIOS, software patches, etc.). The user could then connect the USB-compatible storage device to the USB port 100 on the remote control 70 and download the data thereto, where it may be used by the remote control 70 or transmitted to a PO device in communication therewith.

Another PO device, in the form of a data transfer device 105, is shown in FIG. 4. The data transfer device 105 includes the communications module 5 of FIG. 1, but could also include a communications module having a power supply, such as the communications module 5' of FIG. 2b. The communications module 5 is connected to a host board 110. The host board 110 may include other components that are provided to perform or permit various data transfer functions. For example, and without limitation, the host board 110 may include one or more components for converting wireless transmissions from a PO device into serial communications compatible with another device such as a PC or PDA.

A USB connector 115 is provided and preferably integrated to the host board 110. The USB connector 115 allows the data transfer device 105 to interface with any USB port of another USB-compatible device. Although not shown, the data transfer device 105 preferably also includes a housing for enclosing at least the host board 110 and communications module 5.

PO devices of the types contemplated by the present invention, especially those with sensors, may collect enormous amounts of data. While it may not be practical or economic to provide each PO device with the ability to store days or weeks of real time data, there are times when having the ability to do so would be useful.

However, storage and/or downloading of this data can be difficult due to the shear amount of data that can be generated, and/or due to the fact that the ultimate user of the data may not be the patient to which the device is attached. Therefore, it is desirable to have a method of downloading and storing data from a PO device. One such method employs a data transfer device that may closely resemble a remote control device in design. Typically, however, such a data transfer device would have considerably more memory capacity than would a remote control. Such a data transfer device may also be provided with one or more sensors not commonly found on a remote control.

Such a data transfer device could be carried by a patient during normal activities and could be programmed or signaled to wake up periodically in order to download data from a PO device(s) of interest before the memory capacity of the PO device(s) is exhausted. In one scenario, a clinician could give a data transfer device to a patient to take home and carry. The data transfer device would be placed in wireless communication with a PO device(s) of interest, as described above. The patient would then return with the data transfer device after a suitable period of time so that the clinician could evaluate the patient's usage of the PO device(s). In another scenario, the clinician could simply mail the data transfer device to a patient in the field and, after suitable data recording, the patient could return the data transfer device to the clinician in the same manner. The clinician could then analyze the data on the data transfer device to evaluate the function of the PO device(s) and/or PO system without requiring the patient to physically visit the clinician's office.

As mentioned above, it may be desirable for the data transfer device to collect data that would not normally be required by the PO device being monitored. One example might be the use of data transfer device to verify that the use of a vacuum suspension system has in fact improved the level of function of a patient. In this case, the data transfer device could be equipped with inertial sensors to allow it to measure cadence and usage information about the patient before and after the vacuum system was enabled. Thus, the cost of equipping multiple PO devices with sensors that might never be used can be avoided by instead placing the inertial sensors on such a data transfer device.

Such a data transfer device could actually be a flexible remote control device equipped with the ability to plug in a sensor and/or memory upgrade that would allow the remote control to perform data logging functions. In this way, a clinician could mail a patient the expansion parts necessary to convert an existing remote control and ask the patient to connect them to their own remote control device. Once the required data collection process is complete, the patient would simply remove the expansion parts and mail them back to the clinician for analysis.

Therefore, such an application is an excellent example of the flexible design philosophy associated with devices and systems of the present invention. Essentially any PO device equipped with a communications module can be made to perform a very wide range of tasks through simple reconfigurations of the module and its associated hardware.

Timing

There are an almost unlimited number of PO system configurations possible using any number of PO devices of the present invention. As discussed above, a method of enforcing communications timing is desirable in order to prevent communication problems and to ensure that the transmitted data is useable for controlling the devices of the PO system. A preferred, but not solitary, method of enforcing timing while also minimizing power consumption is a system based on the concept of time slicing. This timing methodology may provide significant benefits when used as a PO system communication protocol.

Figure 5:
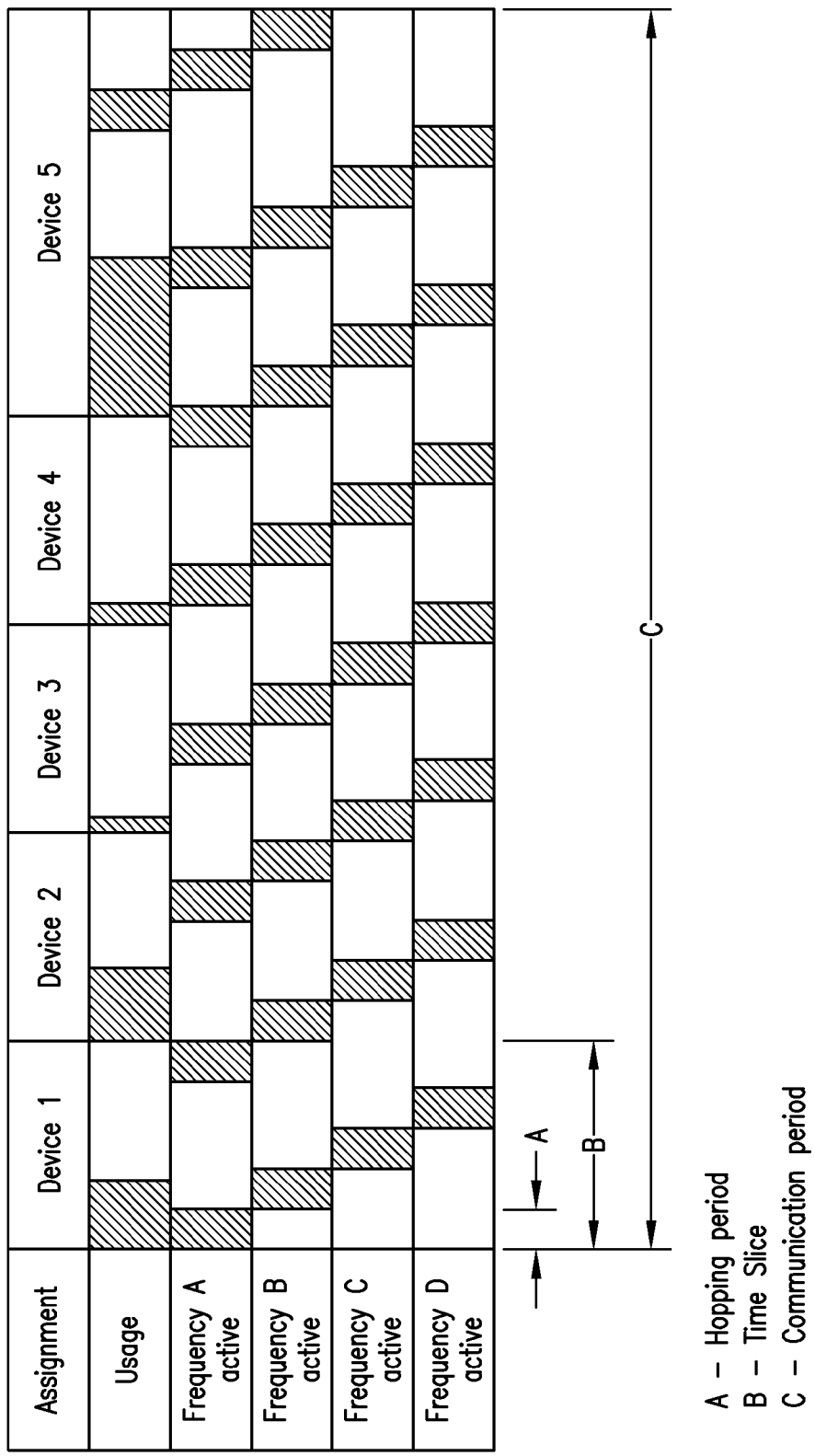
FIG. 5 graphically depicts a number of PO devices operating under a time slice communication protocol according to the present invention.

FIG. 5 graphically illustrates how time is broken up under such a protocol into a number of periods (C) which, in this particular example, are assigned to PO Devices 1-5. Other numbers of devices may, of course, be present in other embodiments. The total period time depends on the update rate necessary for the given PO system. This time period is then broken up into a number of time slices (B) according to the bandwidth required by each PO device pairing.

At the start of each time slice, the transceiver of the primary PO device initiates communication with the secondary PO device assigned to that time slice. Because both PO devices know when the communication is scheduled to occur, neither PO device need be active until it is time for the slice. Further, once the necessary communication is complete, both PO devices can shut down until their next appointed communication with another PO device.

Inside of each of these periods, a given PO device will have assigned communications times that are set aside for communication between it and another PO device. The two PO devices can then use as much, or as little of this time as is necessary to transmit the information that they have accumulated since their time slice in the previous communication period. As explained in greater detail below, if this process is implemented using frequency hopping, it is then possible to have multiple pairs of PO devices talking simultaneously. This resulting communications protocol is robust, time determinant, power efficient, and allows for high data bandwidth.

Frequency hopping permits PO devices operating under the above described time slice protocol to continuously switch operating frequencies. In this way, a PO device has multiple chances within each time slice to establish communication in the event of interference. As shown in FIG. 5, if the frequency hopping period (A) is short enough to allow numerous hops inside of a single communication slice, every communication in every time period can be tried on multiple frequencies to ensure that the communication will reach its destination. Also, unless an outside party knows of the hopping sequence and timing, communication interception will be very difficult if not impossible.

In addition to these obvious advantages, frequency hopping also allows multiple communications channels to be open in the same PO system. In this manner, bandwidth in the PO system becomes a function of the number of PO devices present and the number of hopping frequencies used—not just the number of time slices available.

Another significant advantage to using frequency hopping is shown in FIG. 6. Specifically, multiple PO devices can communicate simultaneously without interfering with each other. While it is possible to simply let each PO device pair hop randomly and recover from the occasional collisions, this has obvious negative consequences for communication reliability and power consumption. Efficiency and reliability are maximized if the frequencies at each hop are allocated so that each pair of PO devices is on a different frequency. This can be accomplished in a number of ways. A brute force method is to simply assign a completely separate set of frequencies to each PO device pairing. However, this greatly reduces the number of frequencies available in a given bandwidth for a given pair of PO devices. Instead, and as shown, a preferred method is to use the same frequency sequence for all PO device pairs, but to provide an offset of several frequencies so that communications never collide.

Topology

Figure 7:
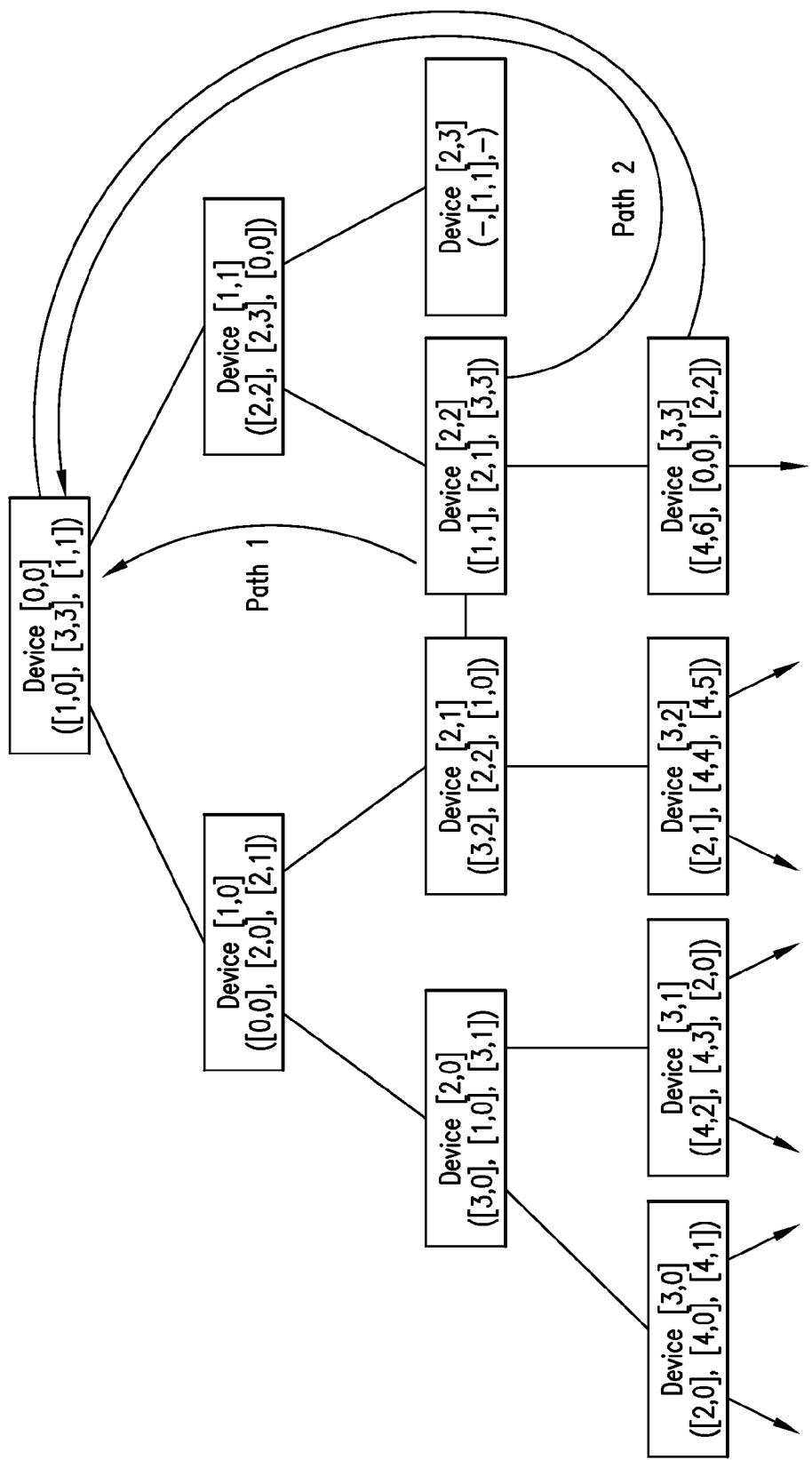
FIG. 7 is a schematic representation of a communication hierarchy that may exist between multiple PO devices of a PO system of the present invention.

One possible and interesting implementation of a PO system of the present invention is one used by a patient with multiple prosthetic limbs. A communication topology suitable to such a PO system is schematically represented in FIG. 7. In such a configuration, one PO device acts as a top level primary control device, which might, for example, be responsible for two prosthetic limbs (e.g., prosthetic legs). Thus, the top level primary PO device could allocate time slices to each of the prosthetic limbs and communicate with the limbs every communication period. In addition to these timed communication periods, each of the PO devices could have a subsystem that operates on either an orthogonal set of frequencies, or a predetermined cycle of frequencies that is offset from the hopping sequence used for the main system. In this manner, a top level primary PO device could receive the pertinent information from an immense number of lower level (subordinate) PO devices channeled thereto through subsystems and either pass along or, perhaps, process and then pass along information about their respective systems and subsystems.

In this topology, each PO device can function as either a primary communication device, which essentially controls the timing of the communications on that channel, or as a secondary device that follows the timing enforced by the associated primary device. PO devices on intermediate levels in the chart of FIG. 7 change modes depending on whether they are talking to a higher or lower level PO device.

For clarity, each PO device is referenced in FIG. 7 by labels corresponding to [Level, Device Number]. There is one top level primary PO (control) device, device [0, 0], which enforces the timing for its network. Each of the secondary PO devices in the second level of the communication chart [1, 1]-[1, n] then enforces the timing of the top level PO device on its sub-network. These [2, n] PO devices then enforce the timing down to their respective sub-networks.

Each PO device accepts the enforced timing while in secondary mode and then enforces it to its secondary PO devices. In this way, the timing throughout the network is referenced back to the [0, 0] PO device. Also, because all timing is referenced back to the [0, 0] PO device, any two PO devices can communicate. In this manner, it is possible to have lower level PO devices communicate directly to the [0, 0] PO device, or to PO devices on other sub-networks. This could be done to reduce communication time between two PO devices, or to open up multiple channels of communication between any two PO devices to add reliability.

Another beneficial function of the topology of FIG. 7 is that all the PO devices have their time slice timing referenced to a single source, in this case, the PO device labeled as [0, 0]. Therefore, in principal, any two PO devices can communicate as long as the same time slice is assigned to both PO devices for the communication.

This is illustrated, for example, by the level 2 PO devices of FIG. 7. Specifically, this is shown by the communication that occurs between level 2 devices [2, 1] and [2, 2]. Were these two PO devices not capable of direct communication, messages therebetween would have to pass through PO devices [1, 0], [0, 0], and [1, 1]. Not only would this result in a significant increase in bandwidth as the message is repeated time and again, it would also result in a timing delay of 4 time periods between the transmission of a message and its reception. In the case of a real time controller, this is likely unacceptable.

The second example of such a communication link is shown to exist between PO devices [3, 3] and [0, 0]. This additional communication link provides at least two benefits. The first is that the link creates secondary data path between PO devices [2, 2] and [0, 0]. By this secondary data path, a prosthetic communication system becomes redundant and can be self healing in the event of a PO device or communication link failure. A second advantage is that, as in the previous case, PO device [0, 0] has access to data from PO device [3, 3] after a single communication period. As both examples show, time critical data can be linked directly to any device in the system. The only limit is the number of time slices available in a single communication period.

In simple networks, there may only be two levels of PO devices—one primary device at location [0, 0], and one or more secondary devices at [1, 1]-[1, n]. In these cases, the level 1 devices will only function as secondary devices.

In conjunction with the PO devices and other aspects of the present invention, it is also contemplated that once data form a PO device(s) has been collected, transferred, compiled and analyzed, it is possible to create tools or reports to allow the data to be used and communicated. This combination of data collection, data analysis, system configuration and/or programming, and device testing truly allows access and usage of the full capability of the functionality that can now be built into a PO device or PO system.

While certain embodiments of the present invention are described in detail above, the scope of the invention is not to be considered limited by such disclosure, and modifications are possible without departing from the spirit of the invention as evidenced by the following claims:

What is claimed is:

1. An intercommunicating prosthetic/orthotic (PO) device system, comprising:
  a first PO device in the form of an artificial limb component, said first PO device including a communications/control module having communication and control components, said communication and control components mounted to a single board and including at least a transceiver, a microprocessor, and an antenna; and
  a second PO device in the form of an artificial limb component, said second PO device including a communications/control module having communication and control components, said communication and control components mounted to a single board and including at least a transceiver, a microprocessor, and an antenna;

wherein, said PO devices are adapted for wireless and bi-directional intercommunication over one or more communication channels; and wherein, said bi-directional intercommunication is accomplished by a technique selected from the group consisting of time slicing, the use of distinct frequency sets, and the use of temporally shifted frequency sets.

2. The PO device system of claim 1, further comprising a remote control adapted for wireless communication with at least one of said first and second PO devices.

3. The PO device system of claim 2, wherein said remote control is a fob.

4. The PO device system of claim 1, wherein at least one of said PO devices is a prosthetic socket evacuation device.

5. The PO device system of claim 1, further comprising a data transfer device to which at least one of said first and second PO devices may wirelessly transmit data, said data transfer device including a communications/control module having at least a transceiver, a microprocessor, and an antenna.

6. The PO device system of claim 5, wherein said communications/control module of said data transfer device is located within a portable housing connected to a USB interface.

7. The PO device system of claim 1, wherein at least one of said first and second PO devices is adapted to employ frequency hopping within a given communication time slice.

8. The PO device system of claim 1, wherein one of said PO devices acts as a top level primary control device and the other PO device acts as a subordinate device that reports to the top level primary control device.

9. An intercommunicating prosthetic/orthotic (PO) device system, comprising:
a first PO device in the form of an artificial limb component, said first PO device including a common communications module having communication and control components, said communication and control components mounted to a single board and including at least a transceiver, a microprocessor, and an antenna, said first PO device acting as a top level primary control device; and
a plurality of additional PO devices in the form of artificial limb components, each additional PO device including a common communications module having communication and control components that are mounted to a single board and include at least a transceiver, a microprocessor, and an antenna, each additional PO device acting as a subordinate device that reports to the first PO device;
wherein, said PO devices are adapted for wireless and bi-directional intercommunication over one or more communication channels.

10. The PO device system of claim 9, wherein, said bi-directional intercommunication is accomplished by a technique selected from the group consisting of time slicing, the use of distinct frequency sets, and the use of temporarily shifted frequency sets.

11. The PO device system of claim 9, further comprising a remote control adapted for wireless communication with at least one of said PO devices.

12. The PO device system of claim 9, wherein said remote control is a fob.

13. The PO device system of claim 9, wherein at least one of said PO devices is a prosthetic socket evacuation device.

14. The PO device system of claim 9, further comprising a data transfer device to which at least one of said PO devices may wirelessly transmit data, said data transfer device including said common communications module.

15. The PO device system of claim 14, wherein said communications/control module of said data transfer device is located within a portable housing connected to a USB interface.

16. The PO device system of claim 9, wherein at least certain ones of said PO devices employ frequency hopping within a given communication time slice.

17. A method of effecting bi-directional intercommunication between multiple PO prosthetic/orthotic (PO) devices of a PO device system, comprising:
providing a plurality of PO devices in the form of multiple artificial limb components, each PO device including a common communications/control module having communication and control components, said communication and control components mounted to a single board and including at least a transceiver, a microprocessor, and an antenna;
programming said communications/control module to perform one or more functions unique to the PO device to which it is installed;
providing one or more communication channels over which said PO devices may wirelessly and bi-directionally intercommunicate; and
employing one or more communications techniques selected from the group consisting of time slicing, the use of distinct frequency sets, and the use of temporarily shifted frequency sets to ensure uninterrupted intercommunication between PO devices.

18. The method of claim 17, further comprising using a remote control to wirelessly communicate with at least one of said PO devices.

19. The method of claim 17, wherein at least one of said PO devices is a prosthetic socket evacuation device.

20. The method of claim 17, wherein at least certain ones of said PO devices further employ frequency hopping within a given communication time slice.

* * * * *